US00PP28308P3

(12) United States Plant Patent
Zaiger et al.

(10) Patent No.: US PP28,308 P3
(45) Date of Patent: Aug. 22, 2017

(54) INTERSPECIFIC TREE NAMED 'SWEET PIXIE 5'

(50) Latin Name: ***Interspecific prunus* species**
Varietal Denomination: Sweet Pixie 5

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 118 days.

(21) Appl. No.: 14/757,192

(22) Filed: Dec. 3, 2015

(65) Prior Publication Data

US 2017/0164535 P1 Jun. 8, 2017

(51) Int. Cl.
*A01H 5/08* (2006.01)

(52) U.S. Cl.
USPC ..... Plt./180

(58) Field of Classification Search
USPC ..... Plt./156, 180
See application file for complete search history.

*Primary Examiner* — Susan McCormick Ewoldt
*Assistant Examiner* — Karen Redden

(57) ABSTRACT

A new and distinct variety of interspecific tree (Interspecific *Prunus* species). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of medium size fruit.
3. Fruit with very good flavor and eating quality.
4. Fruit with an attractive red skin color.
5. Fruit with a high degree of soluble solids (Brix) of 23.1°.

1 Drawing Sheet

Botanical designation: Interspecific *Prunus* species.
Variety denomination: 'Sweet Pixie 5'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein 'Black Kat' Interspecific (U.S. Plant Pat. No. 13,134) and the proprietary non-patented interspecific seedlings '301LP509', '178LM244', '82EG198', '104EB90' and the non-patented apricot seedling '1A77'.

STATEMENT REGARDING FEDERALLY SPONSORED RESEARCH AND DEVELOPMENT

Not applicable.

ORIGIN OF THE VARIETY

The new and distinct variety of interspecific tree was originated by us from crosses of *Prunus salicina, Prunus avium* and *Prunus armeniaca* in our experimental orchard located near Modesto, Calif. as a first generation cross between our proprietary non-patented interspecific seedling '301LP509' and the apricot seedling '1A77'. The seed parent '301LP509' is an open pollinated seedling selection from our proprietary non-patented interspecific seedling '178LM244' which is a seedling from a first generation cross between our proprietary non-patented plum seedling '82EG198' and the proprietary non-patented cherry seedling '104EB90'. The pollen parent '1A77' originated from apricot seedling of unknown parentage. A large number of these first generation seedlings were budded onto older established trees of 'Nemaguard' Rootstock (non-patented) to enhance earlier fruit production. Under close and careful observation the present budded seedling exhibited desirable tree and fruit characteristics and was selected in 2009 for additional asexual propagation and commercialization.

ASEXUAL REPRODUCTION OF THE VARIETY

In 2009 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree, which consists of Plum, Cherry and Apricot has vigorous, upright growth and is a regular and productive bearer of medium size fruit with an attractive red skin color. The fruit is further characterized by its firm flesh, very good flavor and eating quality. In comparison to its seed parent (301LP509) the new variety has a winter chilling requirement of 750 hours compared to 100 hours. In comparison to the pollen parent (1A77) the fruit of the new variety has red skin compared to orange. In comparison to the commercial variety 'Black Kat' Interspecific (U.S. Plant Pat. No. 13,134) the fruit of the new variety is approximately 28 days earlier in maturity and has semi-red flesh compared to yellow.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright, usually pruned to vase shape.

*Branch habit*.—Upright, crotch angle approximately 30°, increases with heavy crop load.

*Productivity*.—Productive, thinning and spacing of fruit necessary for marketable size fruit. Number of fruit set varies with climatic conditions during blooming period.

*Bearer*.—Regular, has had adequate fruit set 4 consecutive years. No alternate bearing observed.

*Fertility*.—Self-sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 750 hours at or below 45° F.

Trunk:

*Size*.—Large, average circumference 50.8 cm at 25.4 cm above ground on a 6 year old tree.

*Stocky*.—Medium stocky.

*Texture*.—Medium shaggy, roughness increases with age.

*Color*.—Varies from 10YR 4/2 to 10YR 5/2.

Branches:

*Size*.—Medium. Average circumference 18.8 mm at 1.2 meters above ground. Crotch angle approximately 30°, increases with heavy crop load.

*Surface texture*.—New growth relatively smooth. Mature growth medium rough, roughness increases with age.

*Lenticels*.—Average number 5 in a 25.8 square cm area. Average length 3.1 mm. Average width 1.9 mm. Color varies from 7.5YR 5/8 to 7.5YR 4/8.

*Color*.—New growth varies from 5GY 5/6 to 5GY 5/8. Mature growth varies from 10YR 3/2 to 10YR 2/2, varies with age of growth.

Leaves:

*Size*.—Medium. Average length 102.6 mm. Average width 60.8 mm.

*Form*.—Ovate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Large. Average length 18.0 mm. Average width 1.8 mm. Surface — lightly pubescent. Longitudinally grooved. Color varies from 5GY 6/6 to 2.5YR 3/4.

*Glands*.—Type — globose. Size — small. Average length 1.1 mm. Average diameter 0.8 mm. Number varies from 4 to 5, average number 4. Located primarily on the upper portion of the petiole, base of leaf blade. Color varies from 5GY 8/6 to 5GY 7/6.

*Stipules*.—Average number 2. Average length 7.8 mm. Edges — pectinate. Color 5GY 7/6.

*Color*.—Upper surface varies from 2.5GY 4/4 to 2.5GY 3/4. Lower surface varies from 7.5GY 4/4 to 7.5GY 4/4. Midvein color varies from 10Y 7/4 to 2.5GY 7/4.

Flower buds:

*Size*.—Medium to large. Average length 9.6 mm. Average diameter 6.1 mm.

*Hardiness*.—Hardy with respect to California winters.

*Density*.—Dense.

*Form*.—Conical, becoming elongated just before opening.

*Pedicel*.—Average length 8.5 mm. Average width 0.8 mm. Surface — glabrous. Color varies from 5GY 8/10 to 5GY 7/12.

*Color*.—N 9.5/(white).

*Number of buds per spur*.—Varies from 7 to 14, average number 10.

Flowers:

*Blooming period*.—Date of First Bloom Feb. 13, 2015. Date of Petal Fall Feb. 23, 2015, varies slightly with climatic conditions.

*Size*.—Medium to large. Average height 10.7 mm. Average diameter 20.4 mm.

*Petals*.—Normally 5, alternately arranged to sepals. Petal apex rounded. Petal base — rounded to truncate. Size — medium. Average length 10.0 mm. Average width 7.4 mm. Form — elliptical. Arrangement — free. Margin — sinuate. Color N 9.5/(white). Both upper and lower surfaces glabrous.

*Sepals*.—Normally 5, alternately arranged to petals. Size — small. Average length 2.9 mm. Average width 2.4 mm. Shape — triangular to ovate. Margin — entire. Both upper and lower surfaces glabrous. Color — upper surface varies from 5GY 7/10 to 5GY 5/10. Lower surface varies from 5GY 6/8 to 5GY 5/8.

*Stamens*.—Average number per flower 39. Average filament length 7.1 mm. On average, the stamens are above the height of the petals. Filament color N 9.5/(white). Anther color varies from 5Y 8.5/4 to 7.5Y 9/4.

*Pollen*.—Self sterile, pollinator required. Color varies from 5Y 8/6 to 7.5Y 8/6.

*Pistil*.—Number — normally 1. Surface — glabrous. Average length 9.4 mm. Position of stigma an average of 0.7 mm below anthers. Color varies from 10Y 8/4 to 2.5GY 8/6.

*Fragrance*.—Heavy.

*Color*.—N 9.5/(white).

*Pedicel*.—Average length 9.6 mm. Average width 0.9 mm. Color varies from 5GY 8/10 to 5GY 7/12.

*Number flowers per flower bud*.—Average number 2, varies from 1 to 4.

Fruit:

*Maturity when described*.—Firm ripe and ready for consumption.

*Date of first picking*.—Aug. 12, 2015.

*Date of last picking*.—Aug. 22, 2015, varies slightly with climatic conditions.

*Size*.—Medium. Average diameter axially 51.8 mm. Average transversely in suture plane 50.6 mm. Average weight 82.4 grams, varies slightly with fertility of the soil, amount of thinning and climatic conditions.

*Form*.—Slightly elongated.

*Suture*.—Nearly smooth.

*Ventral suture*.—Nearly smooth.

*Apex*.—Tip.

*Base*.—Flat.

*Stem cavity*.—Rounded. Average depth 3.0 mm. Average diameter 3.0 mm.

Stem:

*Size*.—Medium. Average length 14.3 mm. Average diameter 2.1 mm.

*Color*.—Varies from 10Y 6/8 to 2.5GY 6/8.

Flesh:

*Ripens*.—Evenly.

*Texture*.—Firm, meaty.

*Fibers*.—Few, small, tender.

*Firmness*.—Good, comparable to other commercial interspecific varieties.

*Aroma*.—Moderate.

*Amydgalin*.—Undetected.

*Eating quality*.—Very good.

*Flavor*.—Very good, good balance between acid and sugar.

*Juice*.—Heavy, enhances flavor.

*Acidity*.—Not available.

*Brix*.—Average Brix 23.1°, varies slightly with amount of fruit per tree and climatic conditions.

*Color*.—Varies from 2.5Y 8/4 to 7.5R 4/10.

*Pit cavity*.—Average length 25.9 mm. Average width 17.3 mm. Average depth 5.3 mm. Color varies from 10R 4/10 to 7.5R 4/10.

Skin:

*Thickness*.—Medium.

*Surface*.—Smooth.

*Bloom*.—Moderate amount, complete coverage.

*Tendency to crack*.—None.

*Color*.—Ground color varies from 10YR 7/8 to 5Y 9/2. Overspread with 5R 3/10 to 7.5YR 7/8.

*Tenacity*.—Tenacious to the flesh.

*Astringency*.—Slight to none.

Stone:

*Type*.—Clingstone, strong adherence to flesh.

*Size*.—Medium. Average length 24.9 mm. Average width 16.3 mm. Average thickness 8.5 mm.

*Form*.—Obovoid.

*Base*.—Flat.

*Apex*.—Pointed. Average length 2.2 mm.

*Surface*.—Pitted throughout. One shallow groove on each side of suture extending from base to apex.

*Sides*.—Unequal, one side extending further from suture plane.

*Ridges*.—Very narrow, small ridge near groove on each side of suture, extending from base to apex.

*Tendency to split*.—None.

*Color*.—Varies from 5YR 5/8 to 7.5YR 6/8 when dry.

Kernel:

*Size*.—Small. Average length 14.0 mm. Average width 8.5 mm. Average depth 4.0 mm.

*Form*.—Ovoid.

*Viability*.—Viable, complete embryo development.

*Skin color*.—Varies from 2.5Y 8.5/4 to 5Y 9/4.

Use:

*Dessert*.—Market — local and long distance.

Keeping quality: Good, held firm in cold storage 3 weeks at 38° to 42° F. without internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

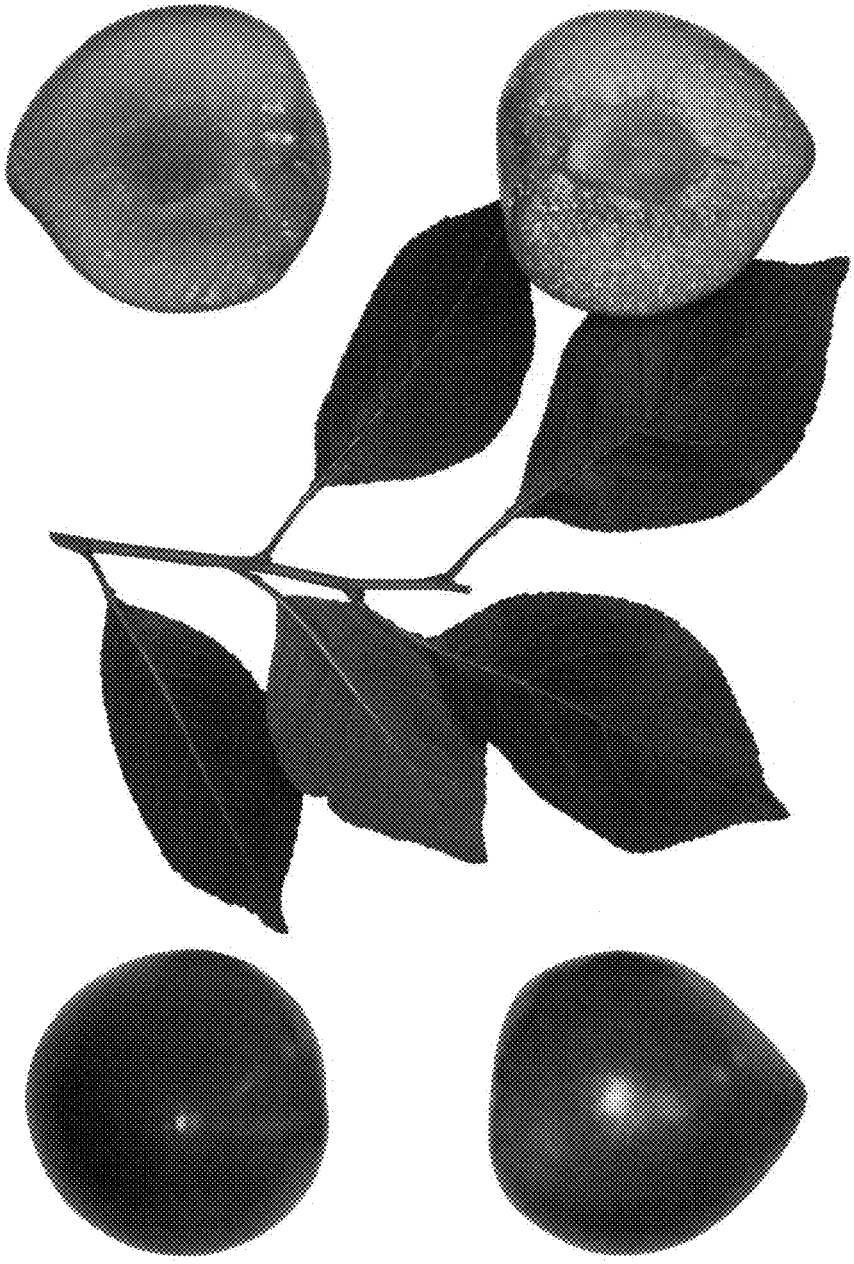

* * * * *